(12) United States Patent
Cawthon et al.

(10) Patent No.: US 10,448,792 B2
(45) Date of Patent: Oct. 22, 2019

(54) HAND HYGIENE

(71) Applicants: Dean Cawthon, Mentor, OH (US); Clifford Cawthon, Mentor, OH (US)

(72) Inventors: Dean Cawthon, Mentor, OH (US); Clifford Cawthon, Mentor, OH (US)

(*) Notice: Subject to any disclaimer, the term of this patent is extended or adjusted under 35 U.S.C. 154(b) by 0 days.

(21) Appl. No.: 14/061,728

(22) Filed: Oct. 23, 2013

(65) Prior Publication Data

US 2014/0110427 A1    Apr. 24, 2014

Related U.S. Application Data

(60) Provisional application No. 61/717,921, filed on Oct. 24, 2012.

(51) Int. Cl.
| | |
|---|---|
| *A47K 17/00* | (2006.01) |
| *E06B 11/08* | (2006.01) |
| *E01F 13/02* | (2006.01) |
| *G08B 21/24* | (2006.01) |

(52) U.S. Cl.
CPC ............ *A47K 17/00* (2013.01); *E01F 13/022* (2013.01); *E06B 11/08* (2013.01); *G08B 21/245* (2013.01); *A61L 2202/14* (2013.01)

(58) Field of Classification Search
CPC ... A47K 5/1217; A47K 17/00; A61L 2202/14; A61L 2/0088; A61L 2/18; A61L 2/26; A61L 2202/10; A61L 2202/15; A61L 2202/16; A61L 2202/17; A61L 2202/25; G08B 21/245; E01F 13/022; E01F 13/06; E06B 11/08; E06B 11/085

USPC .................................. 222/52, 192; 49/31, 381
See application file for complete search history.

(56) References Cited

U.S. PATENT DOCUMENTS

| | | | | |
|---|---|---|---|---|
| 103,523 | A * | 5/1870 | Taylor ................. | B05B 11/3074 137/625.22 |
| 336,327 | A * | 2/1886 | Laska .................. | A01K 63/006 137/131 |
| 1,586,397 | A * | 5/1926 | Bobrick ............... | A47K 5/1204 222/173 |
| 1,726,135 | A * | 8/1929 | Ames ..................... | A47J 31/46 222/130 |
| 1,789,211 | A * | 1/1931 | Benham ............... | B67D 1/0009 222/130 |

(Continued)

FOREIGN PATENT DOCUMENTS

CA            2709200       *   1/2012

*Primary Examiner* — Patrick M. Buechner
(74) *Attorney, Agent, or Firm* — Steven A. Hill, Esq.

(57) ABSTRACT

A system, method, and apparatus for preventing one with dirty hands from entering or exiting an area without first using a hand washing system. Typical uses would be in hospitals, where patients are endangered by health care workers who may propagate microorganisms and thus illness from patient to patient. The subject technology seeks to stop one from passing by having a barrier block passage. Overrides for bypass system on an emergency basis or when hands are otherwise necessarily occupied, such as in carrying a tray or other objects. Sensors detect presence of obstructions in the movement of the barrier. Further, the barrier may be broken should an emergency arise. Current implementation presumes that one's hands are dirty, and thus entry or exit is initially denied. Once hand washing has occurred, then entry or exit is allowed.

1 Claim, 9 Drawing Sheets

(56) References Cited

U.S. PATENT DOCUMENTS

| | | | | |
|---|---|---|---|---|
| 2,118,532 A * | 5/1938 | Widmann | G05D 7/00 | 137/138 |
| 2,914,252 A * | 11/1959 | Sorensen et al. | E03B 9/20 | 222/179 |
| 3,967,478 A * | 7/1976 | Guinn | E05B 1/0069 | 204/248 |
| 4,228,930 A * | 10/1980 | Hogan | F04B 43/1284 | 222/108 |
| 4,406,190 A * | 9/1983 | Mason | B23B 13/027 | 414/17 |
| 4,896,144 A * | 1/1990 | Bogstad | G08B 21/245 | 340/691.6 |
| 2002/0145523 A1 | 10/2002 | Robaey | E03C 1/057 | 340/573.1 |
| 2006/0008379 A1* | 1/2006 | Mielnik | A61L 2/208 | 422/32 |
| 2007/0213877 A1* | 9/2007 | Hart | E05F 15/70 | 700/282 |
| 2009/0051545 A1* | 2/2009 | Koblasz | G08B 21/245 | 340/573.1 |
| 2009/0091458 A1* | 4/2009 | Deutsch | G06F 19/327 | 340/573.1 |
| 2009/0265990 A1* | 10/2009 | Stratmann | A47K 5/12 | 49/31 |
| 2009/0324444 A1* | 12/2009 | Stratmann | G08B 21/245 | 422/28 |
| 2010/0328443 A1* | 12/2010 | Lynam | G06F 19/327 | 348/77 |
| 2011/0025509 A1* | 2/2011 | Brow | A47K 5/06 | 340/573.1 |
| 2011/0163870 A1* | 7/2011 | Snodgrass | A61B 5/1122 | 340/539.11 |
| 2011/0171065 A1* | 7/2011 | Park | A61L 2/22 | 422/33 |
| 2011/0222962 A1* | 9/2011 | Jette | E01F 13/06 | 404/6 |
| 2011/0273298 A1* | 11/2011 | Snodgrass | G08B 21/245 | 340/573.1 |
| 2013/0122807 A1* | 5/2013 | Tenarvitz | H04B 5/0031 | 455/41.1 |
| 2013/0229263 A1* | 9/2013 | Graczyk | G01S 1/70 | 340/10.1 |
| 2014/0059796 A1* | 3/2014 | Boodaghians | A61L 2/10 | 15/339 |
| 2014/0375457 A1* | 12/2014 | Diaz | G06F 19/327 | 340/573.1 |
| 2014/0375458 A1* | 12/2014 | Miller | A47K 5/1217 | 340/573.1 |
| 2015/0033628 A1* | 2/2015 | Barwick | E06B 11/085 | 49/13 |
| 2015/0033629 A1* | 2/2015 | Barwick | E06B 11/085 | 49/13 |
| 2015/0070174 A1* | 3/2015 | Douglas | G08B 21/245 | 340/573.1 |
| 2015/0077258 A1* | 3/2015 | Nelson | G06Q 30/0207 | 340/573.1 |

* cited by examiner

HAND HYGIENE

CROSS-REFERENCE TO RELATED APPLICATIONS

Priority is claimed for provisional application Ser. No. 61/717,921, filing date 24 Oct. 2012, entitled Hand Hygiene System.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The subject technology is in the technical field of hand sanitation assurance and enforcement for protection against contamination, as well as systems, methods, and apparatus making use thereof.

SUMMARY OF THE INVENTION

Hand washing is widely recognized as the primary critical procedure for preventing health care associated infections. Transient microorganisms may reside on hands, being picked up from others, from surfaces, from tools, or from the air. Thus, they can be spread. For people who are already debilitated because of another injury or infection, the introduction of additional microorganisms may cause further damage and may very well kill.

Although common practice today requires the use of gloves to mitigate the spread of microorganisms from person to patient, hand washing remains critical. Indeed, the use of gloves introduces another possible transmission and receiving medium for microorganisms, as gloves must still come into contact with hands as gloves are donned, used, and doffed.

Consider the normal case of a person who works in a health care institution, and who has one or more patients to serve. Service may be medical, a simple delivery of food, delivery of mail, personal hygiene care, simply a visit to check on well-being, social visit, and many other possibilities where one person comes in contact with another.

The hands of such a person in a care giving role should be washed frequently, and always before or after certain events. These events include:

At the start and finish of the person's shift and breaks;
Before and after any direct contact with the patient, with special care required for patients with suppressed immunities;
Between procedures performed on the same patient;
Before and after contact with invasive devices that may come into contact with microorganisms, such as catheters, respiratory equipment;
After contact with body substances, such as blood;
After handling soiled equipment, clothing or bed linen;
After the removal of gloves;
Before and after personal activities, including toilet use, eating, food handling, coughing, and sneezing.

A taxonomy of health care hand washing includes at least social, clinical, and surgical washing. Each requires a different degree of comprehensiveness and resulting cleanliness. Social hand washing is that which is sufficient prior to or following non-invasive social contact. Soap and water are generally sufficient, with care taken not to re-contaminate the hands through post-washing touches of sink handles, soap dispensers, towel dispensers, and other surfaces. Social washing is generally sufficient after a cough or sneeze, before and after meals, and certainly after toilet use. A clinical hand wash is much more rigorous, and is used before and after procedures where the patient is being served in relative isolation. Anti-microbial soap with an antiseptic agent is normally required for clinical hand washing. Surgical hand washing is the most rigorous, as it is required before and after very invasive procedures which of course include surgery. Anti-microbial cleansers with more power agents that used in clinical hand washing are required.

Hand sanitizers are in wide use today and are useful for social and some clinical use where contact with a patient is direct but non-invasive. Typical protocol consists essentially of the following when in the presence of a patient:
1. Wash before touching a patient
2. Wash before any clean or aseptic procedure
3. Wash risk of exposure to bodily fluids
4. Wash after touching a patient
5. Wash after touching patient surroundings A significant risk of harm can be mitigated by adding a step at entry to, and another step at exit from, an area where the patient resides, and applied as an envelope around the typical protocol mentioned above. The resulting protocol is then as follows:
1. Wash hands before entry, to mitigate bringing microorganisms into the area
2. Wash before touching a patient
3. Wash before any clean or aseptic procedure
4. Wash after risk of exposure to bodily fluids
5. Wash after touching a patient
6. Wash after touching patient surroundings
7. Wash hands before exit, to mitigate bringing microorganisms outside of the area The subject technology is a method, system, and apparatus for preventing a person with dirty hands from engaging in activity that may put others in danger. Typical uses would be in hospitals, where patients would be endangered by health care workers who may propagate illness from patient to patient. However, unlike other systems that merely warn or sound an alarm when a person fails to wash hands, the subject technology seeks to stop the person from proceeding with contact by having a barrier block passage. The other systems may even warn or sound an alarm in such a way that only the person whose hands should be washed will know. The subject technology is patient centric, and does not rely on the person to perceive a warning or to act upon it. Furthermore, the patient and others may see entry and exit, and whether hands were washed. The proposed system acts to deter entry or exit, and thus ensures that the person's attention is alerted and that a patient to be served is protected. Overrides allow the care giver to bypass the system on an emergency basis or when hands are otherwise necessarily occupied, such as in carrying a tray or other objects.

Current implementation of the subject technology presumes that the person's hands are dirty, and thus entry or exit is denied from the start. Once hand washing has occurred, then entry or exit is allowed.

DETAILED DESCRIPTION OF THE INVENTION

| Reference Numbers | |
|---|---|
| 100 | hand hygiene device |
| 102 | arm |
| 104 | reservoir |
| 106 | fill tube |
| 108 | fill port |
| 110 | body |
| 112 | hub |
| 114 | release latch |
| 116 | bracket |
| 118 | estop switch |
| 120 | dispense-only switch |
| 122 | indicators |
| 124 | proximity sensors |
| 126 | dispense port |
| 128 | motion sensor |
| 132 | range |
| 150 | graphic |
| 152 | dispense tube |
| 154 | trap |
| 156 | group selector |
| 200 | state diagram |
| 202 | arm-off |
| 204 | arm-down |
| 206 | arm-move-up |
| 208 | arm-up |
| 210 | arm-move-down |
| 212 | sleep |
| 214 | dispense |
| 216 | clean-up |
| | (events) |
| 2001 | arm-removed |
| 2002 | arm-attached |
| 2003 | arm-horizontal |
| 2004 | estop-or-proximity |
| 2005 | switch-active |
| 2006 | no-estop-or-no-proximity-or-timeout |
| 2007 | proximity-and-more-than-zero-group-count |
| 2008 | group-count-zero |
| 2009 | timeout |
| 2010 | wake-up |
| 2012 | clean-up-done |
| 300 | flow chart |
| 302 | start |
| 304 | detect arm position |
| 306 | check latch engaged |
| 308 | engage arm and set light pattern a |
| 310 | obstruction detected |
| 312 | estop pressed |
| 314 | set light pattern b |
| 316 | hand detected |
| 318 | hand-free |
| 320 | set reminder, set light pattern d |
| 322 | disengage arm |

| Reference Numbers | |
|---|---|
| 324 | wait |
| 326 | estop un-pressed |
| 328 | dispense only |
| 330 | dtermine group count |
| 336 | detect passage |
| 338 | sanitize hands |
| 340 | sanitize hands |
| 342 | more hands to sanitize |
| 344 | set light pattern c |
| 346 | timeout |
| 400 | electrical control |
| 402 | electrical controller |
| 404 | reservoir lighting |
| 406 | power |
| 408 | pump interface |
| 410 | arm motor |
| 412 | arm communication and power port |
| 500 | arm control |
| 502 | arm controller |
| 506 | wireless interface |
| 508 | accelerometer |
| 510 | proximity sensors |
| 512 | obstruction sensors |
| 514 | approaching object sensors |
| 516 | lighting array |
| 518 | estop switch interface |
| 520 | dispense-only switch interface |
| 522 | group selector interface |

Figure 1:
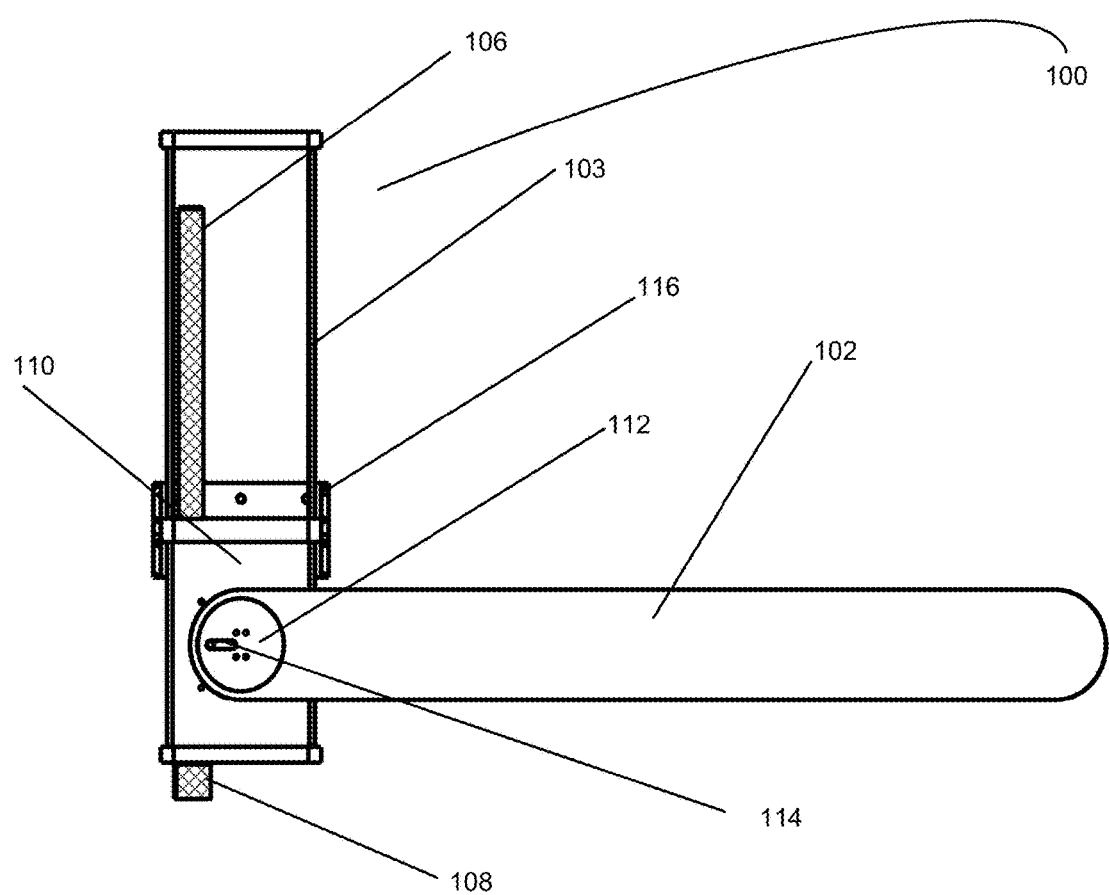
FIG. 1 shows the subject technology from a front view.

FIG. 1 shows a front view of the hand hygiene device 100, comprising a body 110, a reservoir 104 attached to the body 110, an arm 102 that rotates about a hub 112, the hub 112 attached to the body 110, a release latch 114 for releasing the arm 102, a fill tube 106, and a fill tube port 108. The reservoir 104 would contain sanitizing fluid to be used for sanitation. It would be transparent or otherwise configured so that one may see the level of fluid in the reservoir 104. Fluid would enter the reservoir 104 through the fill tube port 108 and the fill tube 106, and would be dispensed through the arm 102. A bracket 116 is attached to the body 110 so that the hand hygiene device 100 may be attached to a wall or other structure so as to manage passage of care givers into or out of an area. The arm 102 is shown in position to block passage, which is normal position. The arm 102 is easily breakable, as may be required in an emergency. And, the arm 102 is easily released via the release latch 114, also as required in an emergency.

Figure 2:
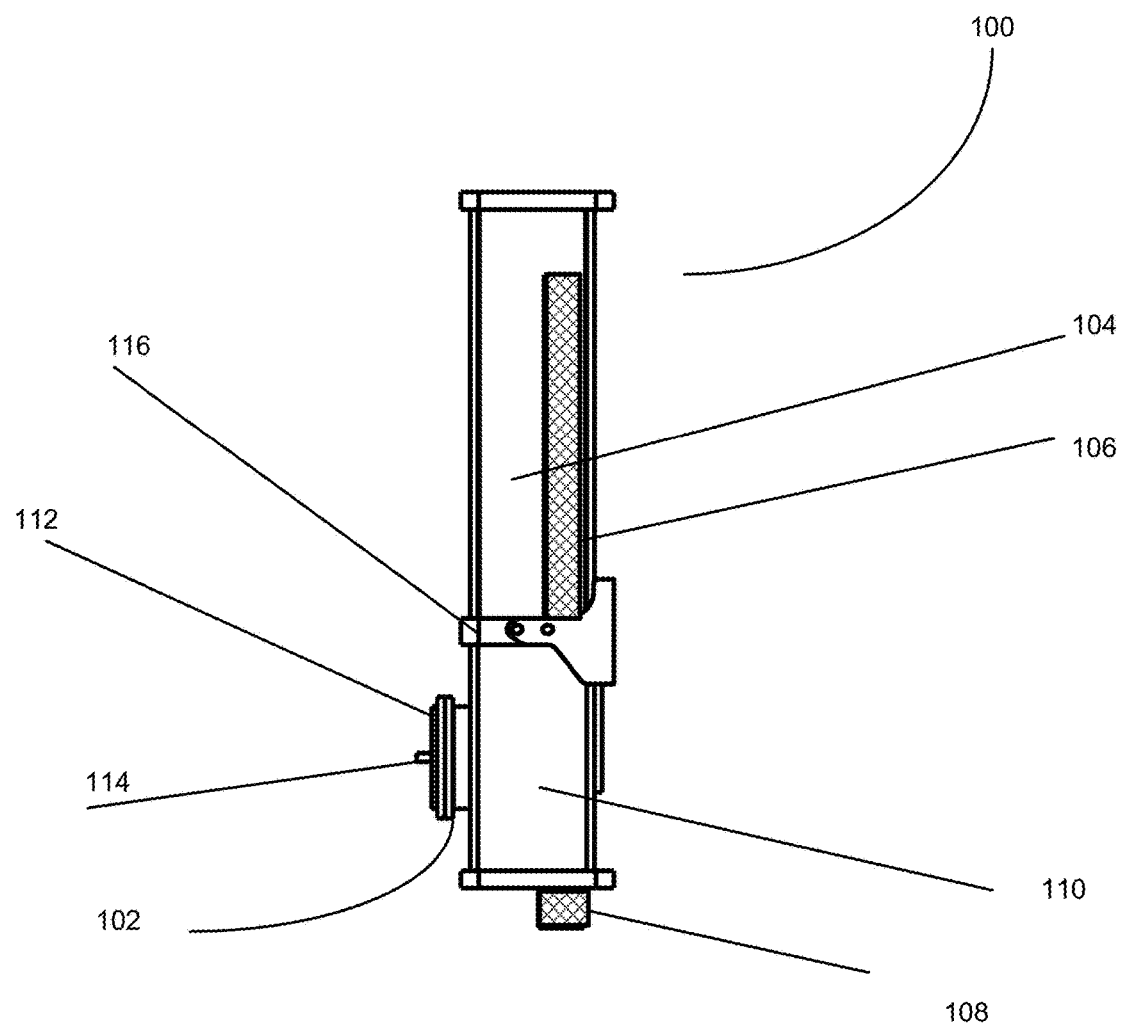
FIG. 2 shows the subject technology from a side view.

FIG. 2 is a side view of the hand hygiene device 100, with the arm 102 in blocking position, although not easily seen in FIG. 2.

Figure 3A:
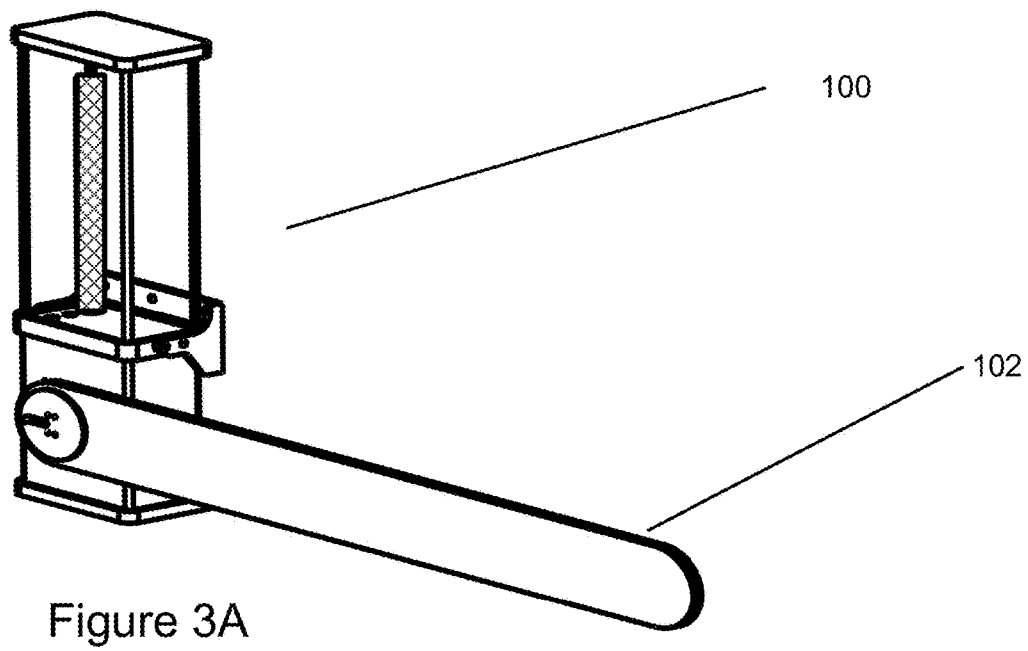
FIG. 3A is a perspective view, with a barrier tending to prevent passage.

FIG. 3A is a perspective view of the hand hygiene device 100, again with the arm 102 in blocking position.

Figure 3B:
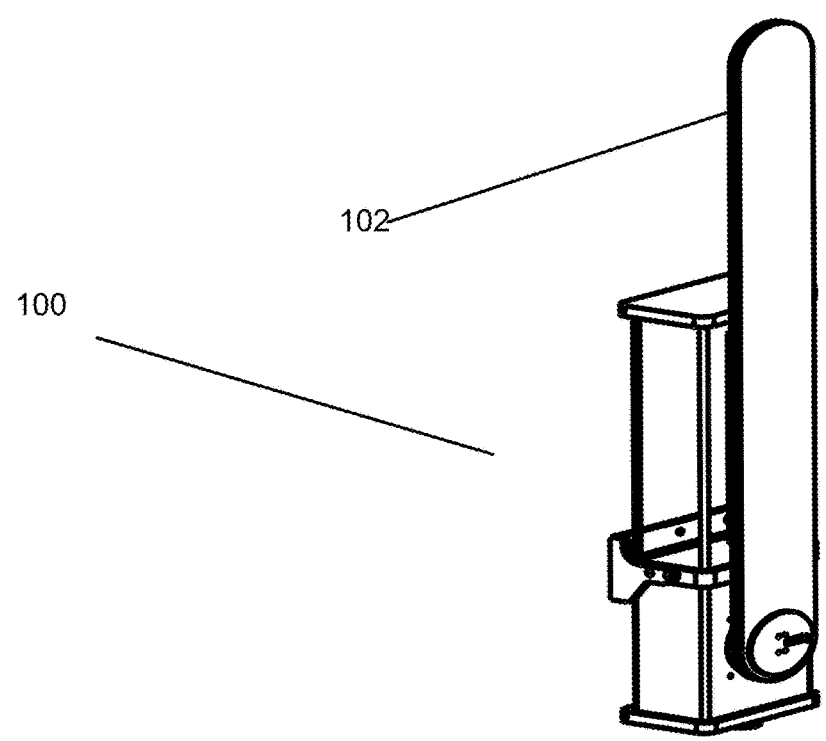
FIG. 3B is a perspective view, with the barrier tending to allow passage.

FIG. 3B, however, is a perspective view showing the arm 102 in position to allows passage.

Figure 4:
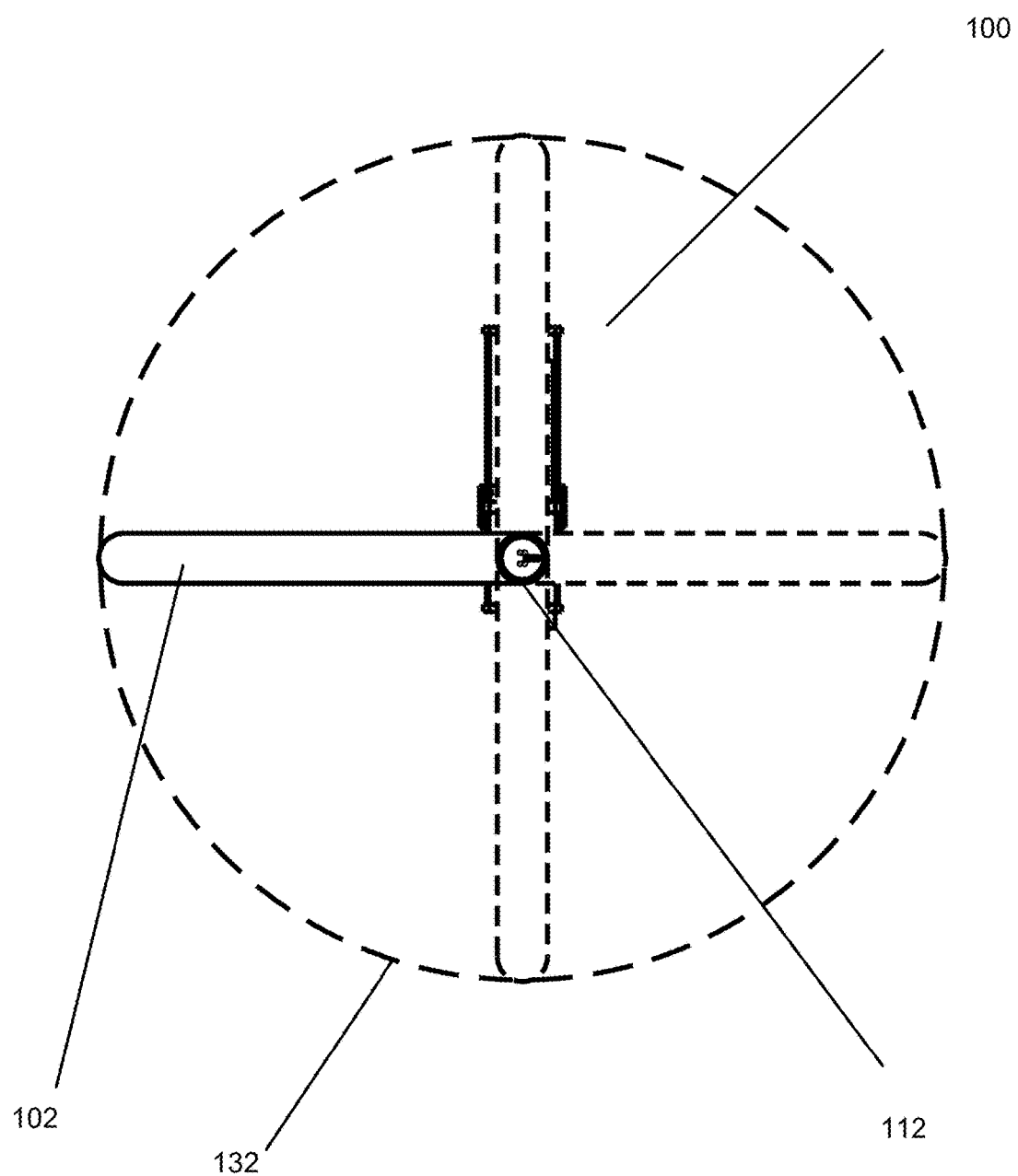
FIG. 4 shows a range of motion of the barrier in preventing or allowing passage, and flexibility in placement of the subject technology.

FIG. 4 shows a range 132 of motion for the arm 102, thus allowing the hand hygiene device 100 to be placed to left, right, center, top, and other locations with respect to a passage way. The range 132 of motion allows the arm 102 to be positioned as required to block or allow passage, based on placement of the hand hygiene device 100.

Figure 5:
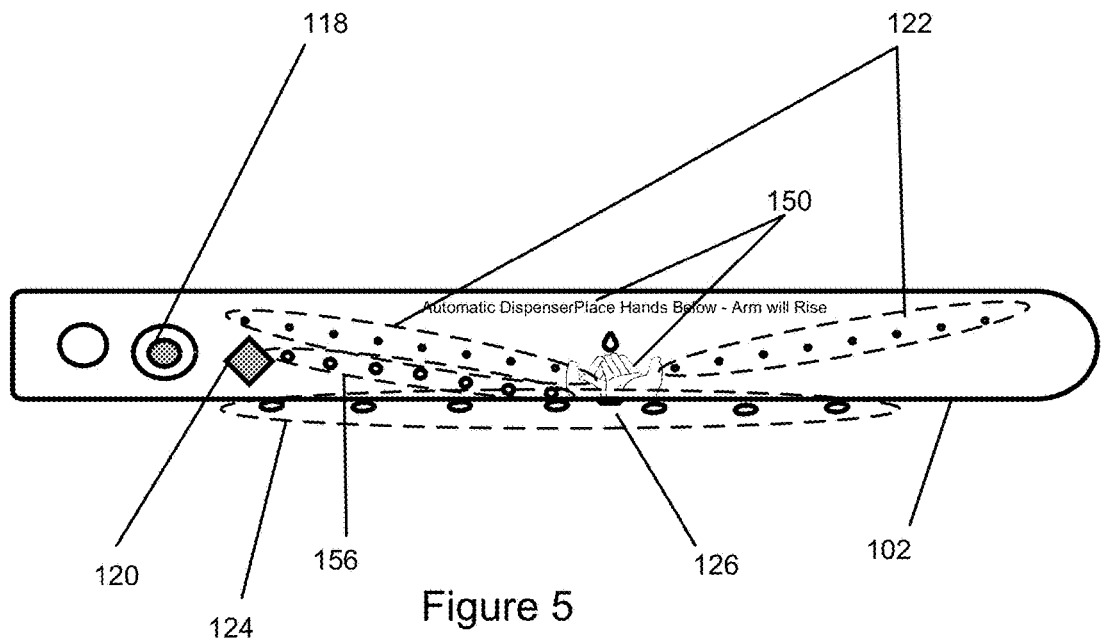
FIG. 5 provides shows controls, graphics, and indicators.

FIG. 5 shows additional detail of the arm 102 exterior. An estop switch 118 is deployed allowing passage on an emergency basis. The estop switch 118 is used to move the arm 102 to allow passage without regard to hand washing events. Once the emergency passes, then the arm 102 is returned to normal, blocking position.

A dispense-only switch 120 allows a care giver to sanitize hands while the arm 102 is in blocking position, as may be required during care giving procedures after the care giver attained passage. An array of indicators 122, which may be light emitting diode (LED) or other illuminators direct the care giver where to place hands in order to receive sanitizing. Further, the array of indicators 122 may be capable of displaying various colors and in various arrangements to display a variety of messages to the care giver. An array of proximity sensors 124 detect the presence of an object, such as an hand, an obstruction, or people passing close by. To allow an enumerated group to pass, a care giver may use a group selector 156 to indicate how many individuals to allow passage. In such case, the hand hygiene device 100 will dispense through arm 102 the number of units of fluid equal to the group number and then raise arm 102 once to allow the group to pass and can then count the number of individuals who pass through before lowering the arm 102 again. This allows the group to enter without having to wait for the arm 102 to dispense fluid, raise to allow the individual to pass, and then lower after the individual passes, for each individual.

Figure 6:
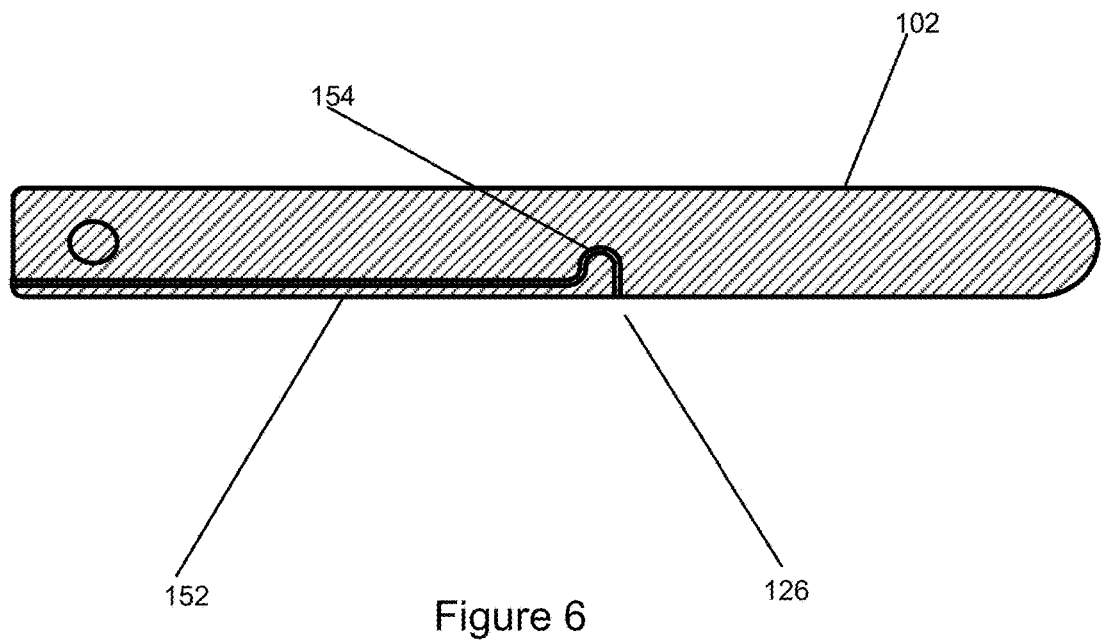
FIG. 6 shows an interior view of one element of the subject technology.

FIG. 6 is an interior view of the arm 102 showing a dispense tube 152 which provides a channel through which sanitizing fluid passes through the arm to the dispense port 126. A trap 154 is provided before the dispense port 126 in order to prevent dripping of sanitizing fluid that remains in the dispense tube 152. The trap 154, as shown in FIG. 6, is configured in a hump shape, so that sanitizing fluid must be forced over the hump and against gravity in order to be dispensed. In this way, dispensing is the result of at least two forces: a) the propelling of the sanitizing fluid over the hump, and b) gravity causing the propelled sanitizing fluid, not already expelled through the dispense port 126, to drop through the dispense port 126. The forces needed to dispense a specific amount of sanitizing fluid and to prevent excess dripping are defined by at least the physical dimensions of the trap 154, the physical dimensions of the dispense port 126, and the physical properties of the sanitizing fluid.

Figure 7:
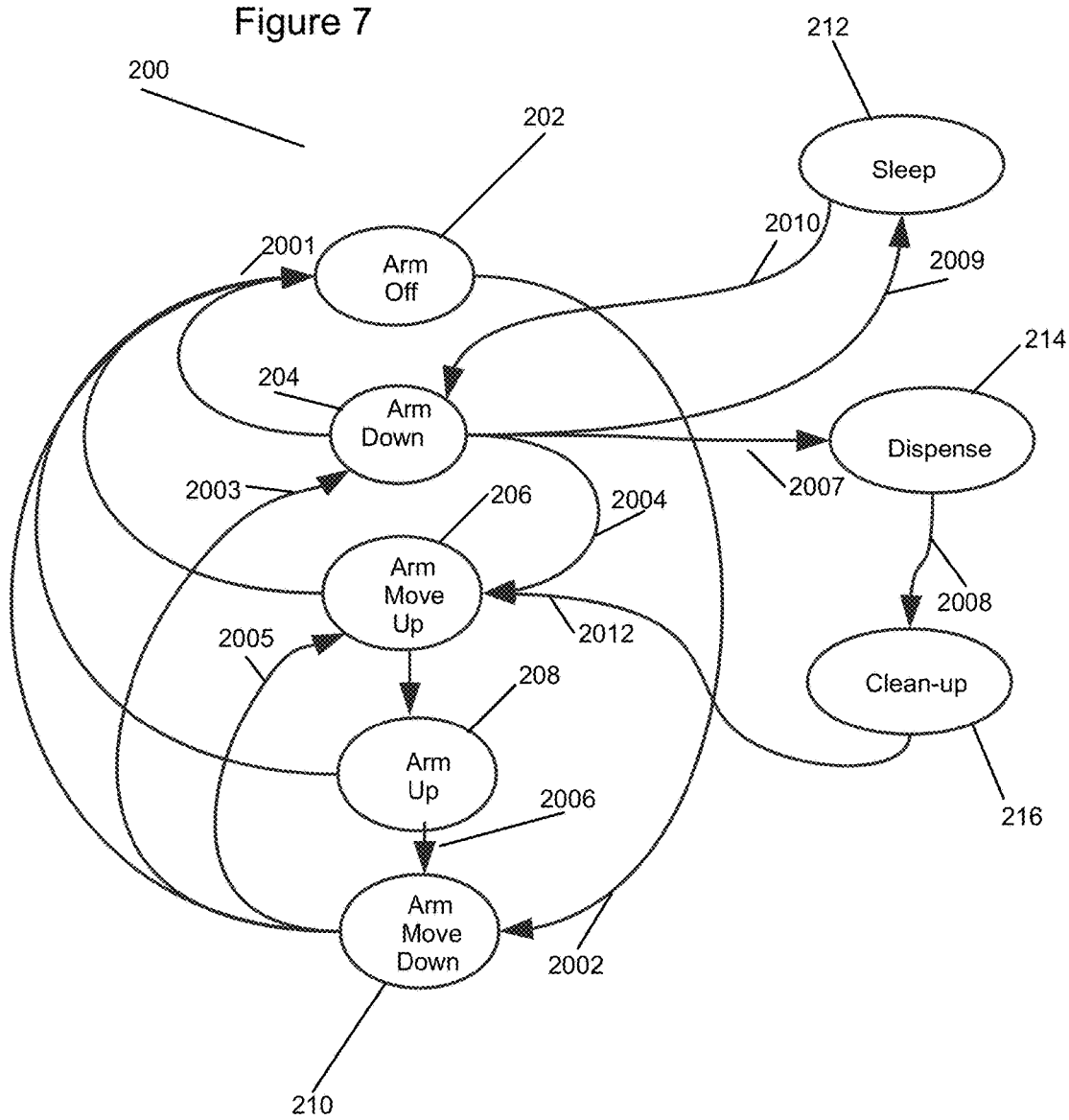
FIG. 7 is a state diagram for the subject technology.

FIG. 7 is a state diagram 200 that shows various operational states of the hand hygiene device 100. The states include arm-off 202, arm-down 204, arm-move-up 206, arm-up 208, arm-move-down 210, sleep 212, dispense 214, and clean-up 216. The states and positions of the arm 102 are all relative. That is to say, whether a particular state or position is blocking or allowing passage depends on other information. Various events cause transitions from state to state. The hand hygiene device 100 is normally in sleep 212 state, to conserve energy. Upon a wake-up 2010 event, the transition is to arm-down 204. Transition from arm-down 204 may be to sleep 212, dispense 214, arm-off 202, or arm-move-up 206 according to the events shown in FIG. 7. Arm-move-up 206 is a transitory state indicating that the arm 102 is in motion. In addition to arrival at arm-move-up 206 via the arm-down 204 state, arrival may be via arm-move-down 210 and clean-up 216 states. Subsequent states to arm-move-up 206 include arm-up 208 and arm-off 202. From arm-up 208 state, two transitions may occur: to arm-move-down 210, which is a another transitory state; or to arm-off 202. From arm-move-down 210, possible transitions include arm-move-up 206, arm-down 204, and arm-off 202. Dispense 214 causes sanitizer to be dispensed. The subsequent state is clean-up 216, which causes sanitizing fluid to be partially sucked back into the dispense tube 152 to prevent dripping. Various transitions, as shown, account for arm-removed 2001, arm-attached 2002, arm-horizontal 2003, estop-or-proximity 2004 (indicating that estop switch was pressed or that a care giver has approached and used hands-free proximity sensor to gain entrance without dispensing), switch-active 2005, no-estop-or-no-proximity-or-timeout 2006, proximity-and-more-than-one-group-count 2007 (a group is passing and care givers are present, but the not all of the selected count have passed by), group-count-zero 2008 (meaning all in the enumerated group have passed by), timeout 2009, and clean-up-done 2012.

Figure 8:
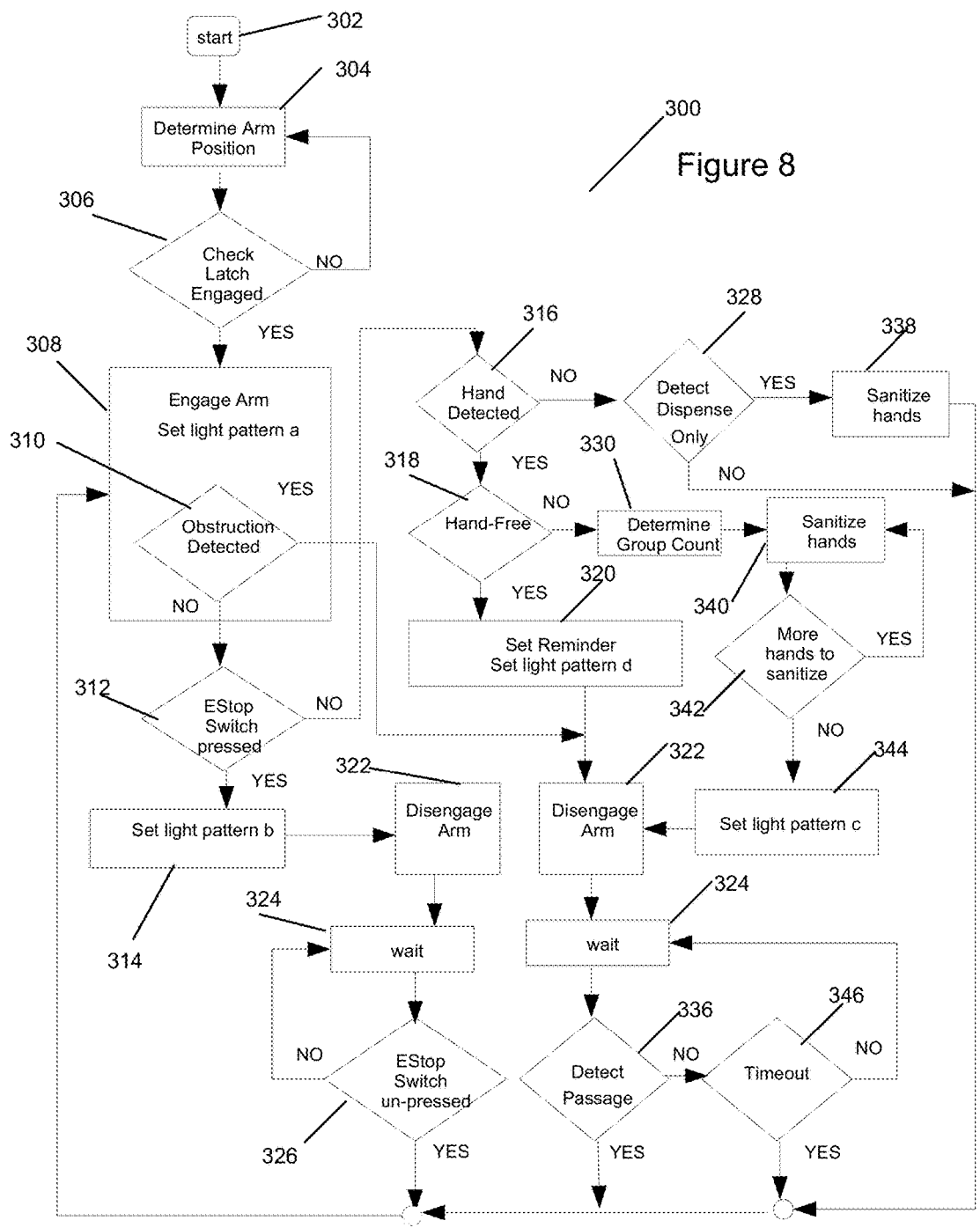
FIG. 8 is a flowchart for one manner of operation of the subject technology.

FIG. 8 comprises a flowchart 300 of various operations and checks. This particular implementation contemplates an array of lights as indicators, to be set to various patterns to convey different information. Indicators 122 are one such implementation of lights. For discussion purposes, these light patterns are designated a through d. From start 302, the hand hygiene device 100 must determine arm position 304, and check latch engaged 306. Upon check latch engaged 306 being "yes," the next operation is engage arm and set light pattern a 308. If no obstruction detected 310, then further check is made for estop pressed 312. If so, flow continues to set light pattern b 314, disengage arm 322, and wait 324 for estop un-pressed 326. Upon estop un-pressed 326, control continues back to engage arm and set light pattern a 308. If, at obstruction detected 310, an obstruction is present, then control flows to disengage arm 322, followed by wait 324 through detect passage 336 or timeout 346. Upon detect passage 336 or timeout 346, control continues back to engage arm and set light pattern a 308.

Suppose, at the test for estop pressed 312, the determination is "no." Control then flows to hand detected 316. From there, two control threads are possible. One includes a test for hand-free 318, which, if true, then proceeds to set reminder and set light pattern d 320 (to remind the care giver to sanitize hands), disengage arm 322, and proceed through wait 324, detect passage 336, and timeout 346 before returning to engage arm and set light pattern a 308.

Hands free operation raises the arm 102 without regard to hand washing events, but does so for a short period. Hands free operation may be initiated by the estop switch 118, and tested at estop pressed 312. This would also be used when a person is carrying a tray or some other object and cannot wash hands while holding the tray or object.

If hand-free 318 is not "yes", then control flows to determine group count 330 and sanitize hands 340 for each care giver according to the count. The other thread includes a test for dispense only 328, which, if true, leads to sanitize hands 338 and, regardless, back to engage arm and set light pattern a 308.

Figure 9:
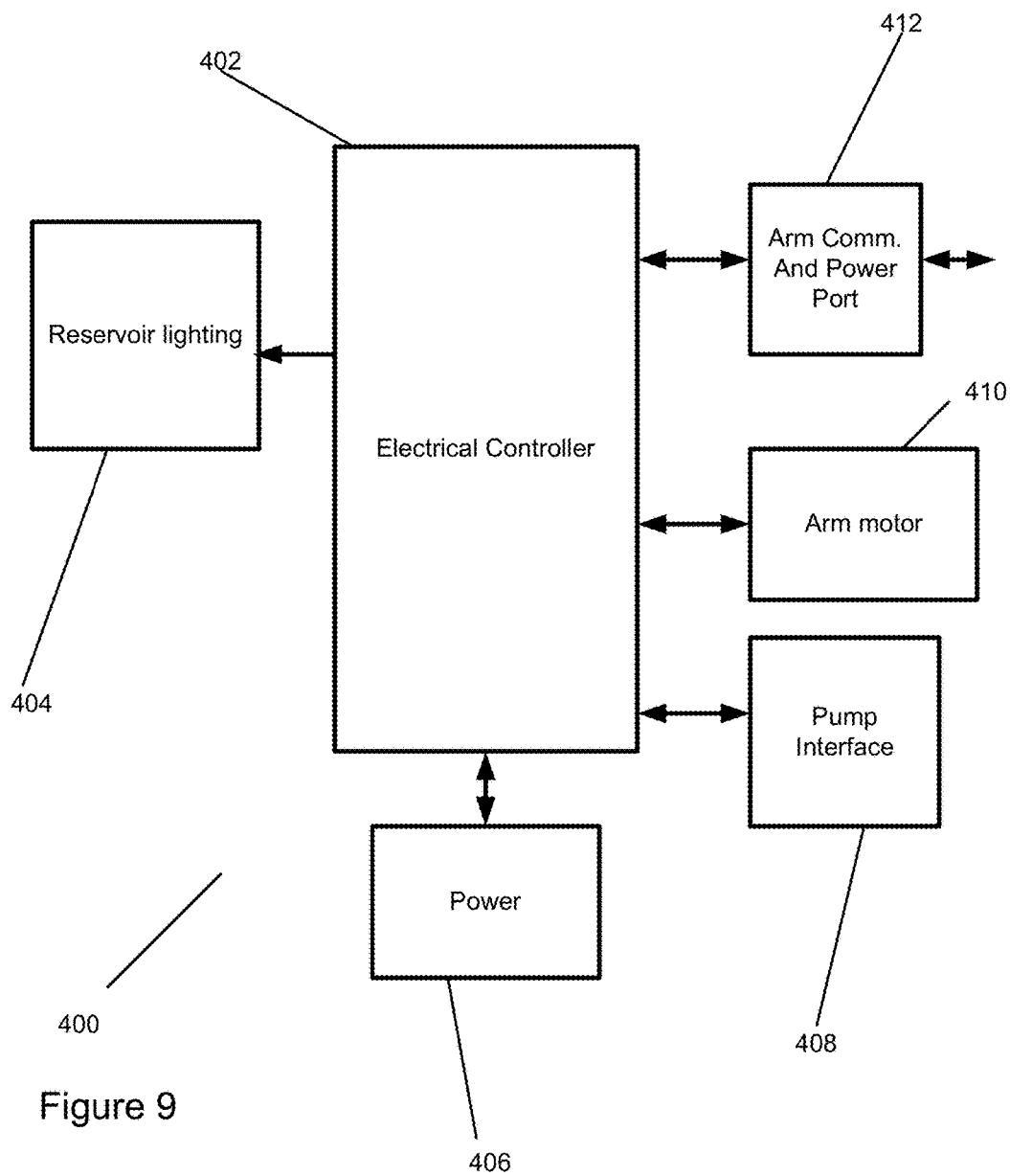
FIG. 9 is a schematic of electrical control.

FIG. 9 shows electrical control 400, comprising an electrical controller 402, power 406, reservoir lighting 404, arm communication and power port 412, arm motor 410, and pump interface 408. The electrical controller 402 is typically a microprocessor or other programmed controlled device, programmed to manage the states and flow control of the hand hygiene device 100. Power 406 includes battery pack, typically chargeable, and electrical current from normal building sources such as wall outlets. The reservoir lighting 404 has aesthetic purpose as well as illuminating the reservoir 103 so that one may easily see the level of the fluid inside. The arm communication and power port 412 is a conduit for communication and electrical current to the arm 102, via the arm control 500 in FIG. 10. The arm motor 410 controls the various positions of the arm 102, as directed by the electrical controller 302. The pump interface 408 manages a pump that delivers sanitizing fluid from the reservoir 103 to the arm 102, via the dispense tube 152, trap 154, and dispense port 126 shown in FIG. 6.

Figure 10:
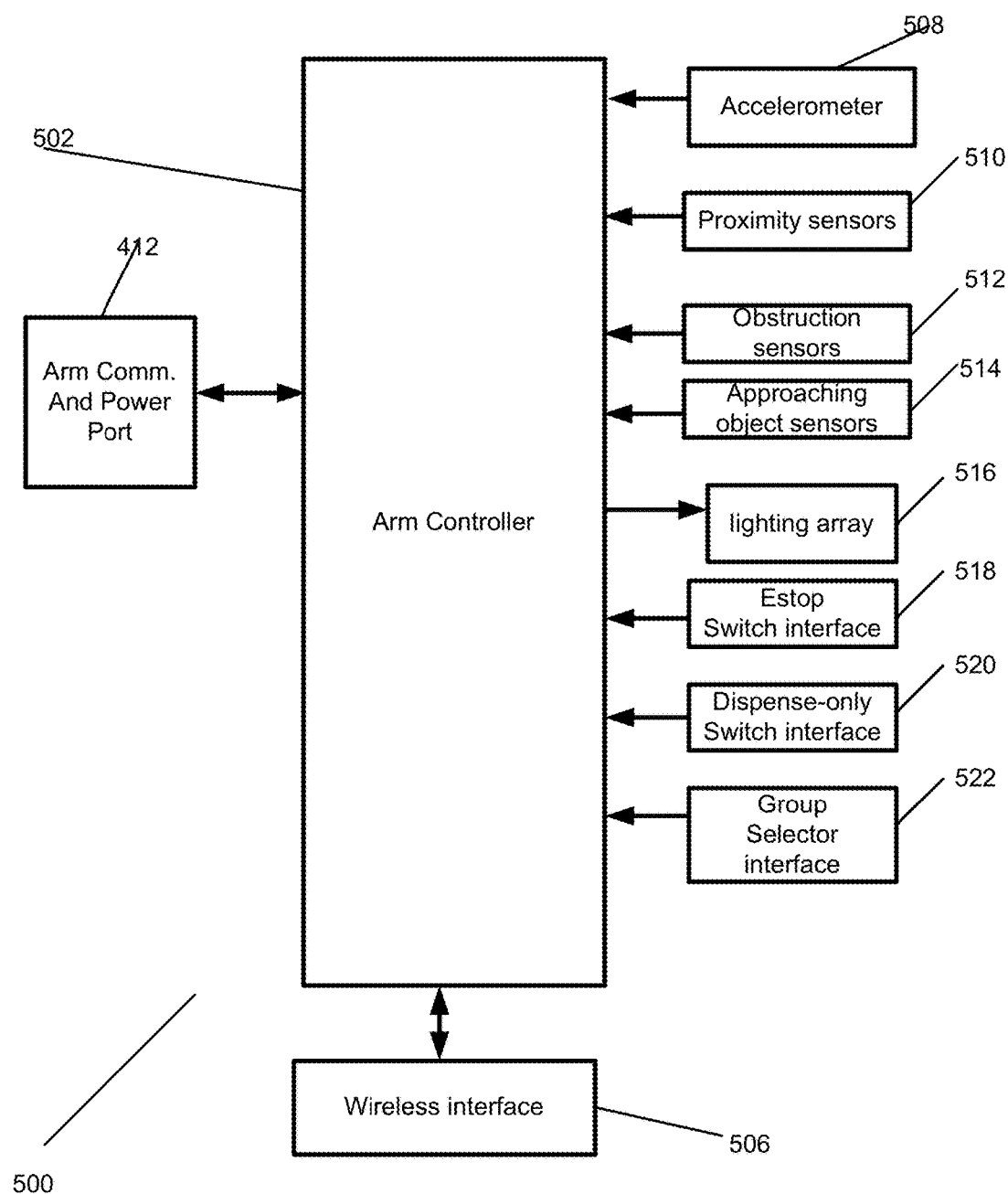
FIG. 10 is a schematic of control at the barrier.

FIG. 10, arm control 500, shows an arm controller 502, the arm communication and power port 412 from FIG. 9, wireless interface 506, accelerometer 508, proximity sensors 510, obstruction sensors 512, approaching object sensors 514, lighting array 516, estop switch interface 518, dispense-only switch interface 520, and group selector interface 522. Wireless interface 506 provides a means to provision the hand hygiene device 100 and to retrieve information from it wirelessly. The accelerometer 508 provides position and motion information concerning the arm 102, so that arm 102 position, speed, direction, and other such aspects may be controlled. Proximity sensors 510 detect hands close to the arm 102 for dispensing sanitizing fluid. Proximity sensors 510 are also used for determining hands free entry: when set for hands free operation, then the presence of a hand will raise the arm 102 without requiring dispensing. Proximity sensors 510 are also used to count care givers as they pass by, with the arm 102 raised, when the hand hygiene device 100 is set to allow a group to pass. Approaching object sensors 514 detect care givers as they approach the hand hygiene device 100. Obstruction sensors 510 are deployed so as to detect an object in the path of the arm 102. The lighting array 516 serves various purposes, as discussed previously. The estop switch interface 518, dispense switch interface 520, and group selector interface 522 convey information about the particular, respective switch setting back to the electric controller 402 via the arm communication and power port 412.

In all modes of operation, the hand hygiene device 100 is operational from front or back, and thus a single deployment may manage passage to and from a given area.

Various additional embodiments of the hand hygiene device include, without limitation:
1. Use of commercially available reservoirs, attachable in place of the reservoir discussed here.
2. Attachment to a doorway or to a movable platform not attached to a doorway.
3. Remote dispensing from a reservoir that is located away from the body and arm, but connected with conduits for fluid.
4. Use of non-fluid sanitizing means, such as forms of light, gasses, and other methods
5. Holographic arm or other display.
6. Remote dispensing from a reservoir that is located at the body and arm, but connected with conduits for fluid to nearby local satellite dispensers in the particular area, such as bedside; each satellite dispenser not being association with passage to or from the area.

While the foregoing written description of the hand hygiene device enables one of ordinary skill to make and use what is considered presently to be the best mode thereof, those of ordinary skill will understand and appreciate the existence of variations, combinations, and equivalents of the specific embodiment, method, and examples herein. The subject technology presented here should therefore not be limited by the above described embodiments, methods, or examples, but by all embodiments and methods within the scope and spirit of the subject technology.

We claim:
1. A device for dispensing sanitizing material to a user, comprising
    a reservoir containing sanitizing material,
    an arm serving to allow or to deny passage of the user,
    a dispense tube being deployed in said arm,
    a dispense port being deployed in said arm,
    a trap comprising a hump deployed between said dispense tube and said dispense port and through which the sanitizing material must pass,
    said dispense tube and said trap forming a conduit between said reservoir and said dispense port,
    said trap further operating with gravity to provide resistance to passage of said sanitizing material;
    a pump to move the sanitizing material to and from said reservoir and through said dispense tube, through said trap, through said dispense port, and to the user;
    electrical control directing said pump to prevent inadvertent and excess delivery of the sanitizing material, said electrical control further comprising causing positive pressure to dispense a predetermined amount of the sanitizing material, the positive pressure being sufficient to move the predetermined amount of the sanitizing material past said trap, and causing negative pressure sufficient to stop dispensing of the predetermined amount of the sanitizing material;
    and electrical control directing said arm to deny passage until the user receives the sanitizing material through said dispense port.

* * * * *